United States Patent [19] [11] 4,054,602
Dhingra [45] Oct. 18, 1977

[54] REMOVAL OF BIS-CHLOROMETHYL ETHER FROM CHLOROACETYL CHLORIDE

[75] Inventor: Yog R. Dhingra, Midland, Mich.

[73] Assignee: The Dow Chemical Company, Midland, Mich.

[21] Appl. No.: 728,103

[22] Filed: Sept. 30, 1976

[51] Int. Cl.$^2$ .............................................. C07C 51/42
[52] U.S. Cl. ............................................. 260/544 Y
[58] Field of Search ................................... 260/544 Y

[56] References Cited
U.S. PATENT DOCUMENTS 3,674,664  7/1972  Larsen et al. ..................... 260/544 Y
3,880,923  4/1975  Scheidmerr et al. ............. 260/544 Y
3,950,415  4/1976  Bressel ............................ 260/544 Y Primary Examiner—Norman Morgenstern
Attorney, Agent, or Firm—G. R. Plotecher

[57] ABSTRACT

Bis-chloromethyl ether is efficiently removed from chloroacetyl chloride by a process comprising contacting the chloroacetyl chloride containing generally about 100 to about 250 ppm bis-chloromethyl ether with hydrochloric acid at a temperature between about 30° C and about 160° C in the presence of a catalytic amount of a Lewis or strong protic acid, such as aluminum chloride or oleum. After a contact time of about 1 hour, the chloroacetyl chloride contains less than 0.3 ppm bis-chloromethyl ether.

10 Claims, No Drawings

REMOVAL OF BIS-CHLOROMETHYL ETHER FROM CHLOROACETYL CHLORIDE

BACKGROUND OF THE INVENTION

1. Field of the Invention

This invention relates to chloroacetyl chloride. In one aspect, this invention relates to chloroacetyl chloride containing bis-chloromethyl ether. In another aspect, this invention relates to a process for removing bis-chloromethyl ether from chloroacetyl chloride.

2. Description of the Prior Art

Larsen et al., U.S. Pat. No. 3,674,664, teach a method of preparing chloroacetyl chloride (CAC) by photochemically oxidizing vinylidene chloride. While this process is industrially attractive, it does produce small (100-250 ppm) amounts of bis-chloromethyl ether (CME), an impurity and a known carcinogen. Since CAC is used as an intermediate in the manufacture of various pesticides and pharmaceuticals, it is desirable to remove the CME from the CAC prior to the latter's use therein. Moreover, higher production costs are experienced because CME-contaminated CAC prohibits CAC recycling due to CME accumulation. Consequently, more waste is experienced.

The preferential removal of CME from CAC is not amenable to most chemical physical separation methods. CAC and CME are similar in their chemical reactivities and physical properties making separation methods, such as selective adsorption, azeotropic or fractional distillation, or complexing, generally ineffective.

SUMMARY OF THE INVENTION

According to this invention, CME is effectively removed from CAC by a process comprising contacting the CAC-containing CME with hydrochloric acid at a temperature between about 30° C and about 160° C, inclusive, in the presence of a catalytic amount of a Lewis acid or strong protic acid. This process does not adversely affect the CAC and the resulting substantially CME-free CAC can either be used as such or flash distilled or treated otherwise to remove the residual catalytic compounds. If flash distilled, the catalytic residue can be recycled.

DETAILED DESCRIPTION OF THE INVENTION

Any suitable Lewis acid or strong, protic acid can be used as the catalyst in this invention. By the phrase "strong, protic acid" is meant an acid that can protonate the oxygen atom of CME. These acids include 96-98 percent sulfuric acid, anhydrous sulfuric acid, oleum, sulfur trioxide, chlorosulfuric acid, p-toluene sulfonic acid, trifluoroacetic acid, phosphoric acid, and strong acid forms of ion exchange resins, such as DOWEX ® MSC-1 (H+) and the like. As used herein, hydrochloric acid and nitric acid are not strong, protic acids. Typical Lewis acids include aluminum, ferric and zinc chloride, boron trifluoride, phosphorus pentachloride, thionyl chloride, etc. Titanium tetrachloride is only marginally effective and is thus disfavored. Aluminum chloride, oleum and anhydrous sulfuric acid are the preferred catalysts.

This invention requires a catalytic amount of the acid catalyst and this amount can vary with the particular catalyst employed. For example, at least about 0.25, and preferably about 1, weight percent (based upon the CAC) is the general minimum amount of a strong protic acid employed, while at least about 0.5, and preferably about 1.5, weight percent is the general minimum amount of a Lewis acid employed. Practical considerations, such as catalyst recovery, economics, and general convenience, are the only limitations on the maximum catalyst amount.

The hydrochloric acid here used can be that inherently present in CAC or can be either introduced into same (generally as an anhydrous gas) or can be generated in situ (generally through the reaction of CAC and water). The HCl inherently present most often is insufficient to substantially eliminate CME therefrom and consequently additional HCl is generally either introduced or generated in situ. The actual amount of HCl inherently present varies from CAC batch to CAC batch and is generally not susceptible to precise measurement. If introduced, said introduction can be made before, concurrent with or after the addition of the acid catalyst. Usually HCl is either sparged directly into the CAC or a CAC-containing reaction vessel is pressurized with same and in a sufficient amount to saturate the CAC.

If generated in situ, additional HCl generally need not be introduced. For example, the water present in 96-98 percent sulfuric acid is sufficient to generate enough HCl to reduce the CME levels to less than 0.2 ppm (if initial CME levels are about 100-250 ppm). However, the in situ HCl formation also generates minor amounts of chloroacetic acid, an impurity. Therefore, in situ HCl formation is disfavored and the use of oleum or anhydrous sulfuric acid and anhydrous HCl is preferred.

Use of various surface-area catalysts, such as retrol clay, various zeolites, silica gels, carbon, and the like, can be combined with the acid catalyst to enhance the rate of reaction between HCl and CME. However, use of a surface-area catalyst alone will not substantially reduce the CME levels.

The typical minimum temperature at which the CME-contaminated CAC is contacted with HCl and the acid catalyst is about 30° C and preferably about 90° C. The typical maximum temperature is about 160° C and preferably about 130° C. Temperatures about 160° C generally result in CAC degradation.

The typical minimum residence time is about 15 minutes and preferably about 30 minutes with the typical maximum residence time about 120 minutes and preferably about 60 minutes. Of course, residence time can vary according to initial CME levels, temperature and catalyst. Reduction in CME levels generally begins within minutes after reaching the typical minimum temperature (described above) and this is especially true if a surface-area catalyst is present.

Pressure is not critical to this invention except for its relationship to temperature. Autogenous pressures are generally sufficient.

Although this invention is generally concerned with removing CME from CAC wherein the initial levels of CME are approximately 100-250 ppm, this invention is adaptable to situations where the initial levels are outside that specified range. If this invention is to be applied to those situations, then catalyst and HCl concentration levels can be adjusted accordingly, if necessary (such adjustments being well within the skill of the ordinary artisan).

The following examples are illustrative of certain specific embodiments of this invention.

SPECIFIC EMBODIMENTS

EXAMPLE 1

CAC (50 g) containing 150 ppm of CME, was sparged with anhydrous HCl gas at room temperature (about 20° C) for about 5 minutes. Oleum (0.5 g) was then mixed into the HCl-saturated CAC. The mixture was heated in a high-pressure glass ampule for about 1 hour at about 120° C. After cooling, gas chromatographic analysis revealed less than a detectable level of CME (with a detection limit of 0.3 ppm).

EXAMPLE 2

CAC samples (28 g each) containing approximately 100 ppm CME were individually contacted with retrol clay, 96 percent sulfuric acid, oleum, and a retrol clay-sulfuric acid combination and subsequently flash distilled. No HCl was added. The results are reported in Table I.

TABLE I
CME DESTRUCTION BY CONTACTING CME-CONTAMINATED CAC SAMPLES WITH RETROL CLAY, $H_2SO_4$, OLEUM AND A CLAY-$H_2SO_4$ COMBINATION FOLLOWED BY SUBSEQUENT FLASH DISTILLATION

| Run | CAC (g) | CME (ppm) | Retrol Clay (g)[1] | 96% $H_2SO_4$ (g) | 20% Oleum (g) | CME-Destruction (%) |
|---|---|---|---|---|---|---|
| Control | 28 | 100 | 2.3 | — | — | 0 |
| a | 28 | 100 | — | 0.6 | — | 80–90 |
| b | 28 | 100 | 2.0 | 0.5 | — | 100 |
| c | 28 | 100 | — | — | 0.5 | 40[2] |
| d | 28 | 100 | — | — | 0.5 | 70[3] |

[1]Oven-dried
[2]After over-night contact at room temperature
[3]Flash-distillation of (?)

Runs c and d illustrate that a partial elimination of CME can be had using only the HCl inherently present in the CAC. However this partial elimination is discernably less than that achieved with the use of additional HCl, generated in situ in runs a and b. The control demonstrates the need of an acid catalyst.

EXAMPLE 3

CME-contaminated CAC was contacted with the below-enumerated substances at the respective temperatures and residence times. CME destruction was monitored by gas chromatography, initial CME levels measured by the Peak Height (Pk Ht) in millimeters and likewise for post-CME levels. Initial CME levels were measured prior to contacting the CAC-containing CME with the various enumerated substances and the post-CME levels were taken after same. In all cases, the CME-contaminated CAC was saturated with HCl. Results are reported in Table II.

TABLE II
CME DESTRUCTION BY CONTACTING CME-CONTAMINATED CAC WITH VARIOUS SUBSTANCES AT VARIOUS TEMPERATURES AND RESIDENCE TIMES

| Run | CAC (g) | Initial CME (mm)[1] | 20% Oleum (g) | $SO_3$ (g) | Silica Gel[2] (g) | Temp. (° C) | Time (hr) | Post CME (mm)[1] |
|---|---|---|---|---|---|---|---|---|
| Control | 42 | 47 | — | — | — | 150 | 18 | NC[3] |
| a | 28 | 50 | 0.55 | — | — | FD[4] | — | 7 |
| b | 42 | 47 | 0.45 | — | — | 125 | 1 | NDL[5] |
| c | 41 | 40 | — | 0.6 | — | FD[4] | — | 12 |
| d | 43 | 36 | — | — | 1.5 | 125 | 1 | 22 |

[1]Peak Height in millimeters
[2]High Purity (100–200 mesh)
[3]No change
[4]Flash-Distilled
[5]No Detectable Level (detection limit of 0.3 ppm)

The partial CME elimination observed in run d is believed attributable to both the slight acidity of the silica gel and the possible adsorption of CME thereon.

EXAMPLE 4

CME-contaminated CAC (70 g) containing HCl was mixed with dried DOWEX ® MSC-1 (H+) (18 g), a strong acid, macroporous styrene divinylbenzene ion exchange resin manufactured by The Dow Chemical Company, and heated for 2 hours at about 120° C. Gas chromatographic analysis revealed about an 80 percent CME destruction (initial CME Peak Height — 44 mm; post-CME Peak Height — 7 mm).

EXAMPLE 5

CAC-containing about 100 ppm CME and saturated with HCl was contacted with varying amounts of oleum and chlorosulfonic acid. The resulting mixtures were heated for 2 hours at about 110° C–115° C and then analyzed by gas chromatography mass spectroscopy for CME. The results are reported in Table III.

TABLE III
CME DESTRUCTION BY CONTACTING CME-CONTAMINATED CAC WITH VARYING AMOUNTS OF OLEUM AND $ClSO_3H$ AT 110° C – 115° C FOR 2 HOURS

| Run | Initial CME (ppm) | 20% Oleum (wt %) | $ClSO_3H$ (wt %) | Post CME (ppm) |
|---|---|---|---|---|
| a | 100 | 1.0 | — | NDL[1] |
| b | 100 | 0.5 | — | NDL |
| c | 100 | 0.26 | — | 19 |
| d | 100 | — | 1.0 | NDL |
| e | 100 | — | 0.5 | 13 |
| f | 100 | — | 0.26 | 25 |

[1]No Detectable Level (detection limit of 0.3 ppm)

EXAMPLE 6

CAC (30 g) saturated with HCl was mixed with some of the residue (3 g) from the flash distillation of the crude reaction product of Example 3, run c. The mixture was heated for 1 hour at 125° C and the crude material subsequently analyzed by gas chromatography. The results showed that the Peak Height for CME was reduced from an initial level of 47 mm to a zero level, i.e., below detection level.

EXAMPLE 7

Residue (0.5 weight percent) from Example 3, run c, was combined with HCl-saturated CAC. The mixture was then heated at 120° C–125° C for approximately 80 minutes with samples removed therefrom at various intervals and analyzed by gas chromatography/mass spectroscopy. The results show the effect of various residence times and are reported in Table IV.

TABLE IV
CME DESTRUCTION AT VARIOUS RESIDENCE TIMES WITH 0.5 WEIGHT PERCENT $ClSO_3$ AS CATALYST

| Residence Time (min) | CME Destruction* (%) |
|---|---|
| 0 | 0 |
| 15 | 50 |
| 30 | 75–80 |
| 45 | 100 |
| 60 | 100 |
| 80 | 100 |

*Detection limit of 0.3 ppm

EXAMPLE 8

CAC (30 g) containing approximately 90 ppm CME was heated for one hour at 120° C–125° C with substantially anhydrous aluminum chloride (0.7 g). Gas chromatography showed no detectable level (<5 ppm) of CME. It is believed that the anhydrous aluminum chloride absorbed trace amounts of water prior to its introduction into the CAC. This water generates enough in situ HCl that, when combined with the HCl inherently present in the CAC, was sufficient to substantially eliminate the CME from the CAC.

EXAMPLE 9

Example 1 was repeated except that the CAC contained about 1000 ppm CME rather than about 150 ppm. Product analysis reported less than 0.3 ppm CME.

It is to be understood that the forms of this invention, herewith shown and described, are to be taken as preferred examples of the same, and that variations can be made without departing from the spirit of the invention or the scope of the adjoining claims.

What is claimed is:

1. A process of removing bis-chloromethyl ether from a mixture comprising chloroacetyl chloride and bis-chloromethyl ether, the process comprising contacting the mixture with hydrochloric acid at a temperature between about 30° C and about 160° C, inclusive, in the presence of a catalytic amount of a Lewis acid or a strong protic acid.

2. The process of claim 1 wherein the hydrochloric acid is anhydrous.

3. The process of claim 2 wherein the Lewis acid is aluminum chloride.

4. The process of claim 3 wherein the aluminum chloride is present in an amount of at least about 0.5 weight percent based on the chloroacetyl chloride.

5. The process of claim 3 wherein the aluminum chloride is present in an amount of at least about 1.5 weight based on the chloroacetyl chloride.

6. The process of claim 2 wherein the strong, protic acid is oleum or anhydrous sulfuric acid.

7. The process of claim 5 wherein the oleum or anhydrous sulfuric acid is present in an amount of at least about 0.25 weight percent based on the chloroacetyl chloride.

8. The process of claim 6 wherein the oleum or anhydrous sulfuric acid is present in an amount of at least about 1 weight percent based on the chloroacetyl chloride.

9. The process of claim 4 wherein the contacting is conducted at a temperature between about 90° C and about 130° C, inclusive.

10. The process of claim 9 wherein the bis-chloromethyl ether is present in the chloroacetyl chloride in an amount between about 100 and about 250 ppm.